US010758206B2

(12) United States Patent
Halmann et al.

(10) Patent No.: US 10,758,206 B2
(45) Date of Patent: Sep. 1, 2020

(54) METHOD AND SYSTEM FOR ENHANCED VISUALIZATION OF LUNG SLIDING BY AUTOMATICALLY DETECTING AND HIGHLIGHTING LUNG SLIDING IN IMAGES OF AN ULTRASOUND SCAN

(71) Applicant: General Electric Company, Schenectady, NY (US)

(72) Inventors: Menachem Halmann, Wauwatosa, WI (US); Alexander Sokulin, Tirat Carmel (IL); Peter Lysyansky, Tirat Hacarmel (IL); Lilach Vanuk, Tirat Hacarmel (IL); Cynthia Owen, Powhatan, AR (US); Eunji Kang, South Lyon, MI (US)

(73) Assignee: GENERAL ELECTRIC COMPANY, Schenectady, NY (US)

( * ) Notice: Subject to any disclaimer, the term of this patent is extended or adjusted under 35 U.S.C. 154(b) by 1104 days.

(21) Appl. No.: 14/870,313

(22) Filed: Sep. 30, 2015

(65) Prior Publication Data
US 2017/0091914 A1    Mar. 30, 2017

(51) Int. Cl.
*A61B 8/00* (2006.01)
*A61B 8/08* (2006.01)
*G06T 7/00* (2017.01)

(52) U.S. Cl.
CPC .............. *A61B 8/4245* (2013.01); *A61B 8/08* (2013.01); *A61B 8/4444* (2013.01); *A61B 8/4483* (2013.01); *A61B 8/463* (2013.01); *A61B 8/467* (2013.01); *A61B 8/486* (2013.01); *A61B 8/5215* (2013.01); *G06T 7/0016* (2013.01);

(Continued)

(58) Field of Classification Search
CPC ..... A61B 8/5292; A61B 8/4444; A61B 8/463; A61B 8/06; A61B 8/12; A61B 8/467; A61B 8/10; A61B 8/468; A61B 8/469; A61B 8/488; A61B 8/4245; A61B 8/486; A61B 8/5215; A61B 8/4483; A61B 8/08; G06T 7/0016; G06T 2207/10132; G06T 2207/30061; G06T 2207/10016
See application file for complete search history.

(56) References Cited

U.S. PATENT DOCUMENTS 6,099,471 A *  8/2000  Torp ........................ A61B 8/08
                                                            600/438
8,914,097 B2   12/2014  Burlina et al.
(Continued)

FOREIGN PATENT DOCUMENTS

WO    2008073560 A2    6/2008

OTHER PUBLICATIONS

Doerschug et al., "Intensive Care Ultrasound: III. Lung and Pleural Ultrasound for the Intensivist", AnnalsATS vol. 10, No. 6, Dec. 2013, pp. 708-712 (Year: 2013).*

*Primary Examiner* — Elmer M Chao
(74) *Attorney, Agent, or Firm* — McAndrews, Held & Malloy, Ltd.; Jacob Groethe; David Bates (57) ABSTRACT

An ultrasound device performs an ultrasound scan to acquire a video clip having images of a portion of a lung. The ultrasound device detects lung sliding in each of the images. The ultrasound device highlights the detected lung sliding in each of the images to generate processed images. The ultrasound device displays at least one of the processed images as one or more of an enhanced B mode image and an enhanced virtual M mode image.

18 Claims, 6 Drawing Sheets

(52) U.S. Cl.
CPC ............... *G06T 2207/10016* (2013.01); *G06T 2207/10132* (2013.01); *G06T 2207/30061* (2013.01)

(56) References Cited

U.S. PATENT DOCUMENTS

2013/0184584 A1* 7/2013 Berkey ................ A61B 8/5292
 600/441
2013/0197370 A1* 8/2013 Burlina ................ G06K 9/4642
 600/476

\* cited by examiner

-- PRIOR ART --

FIG. 4

-- PRIOR ART --

METHOD AND SYSTEM FOR ENHANCED VISUALIZATION OF LUNG SLIDING BY AUTOMATICALLY DETECTING AND HIGHLIGHTING LUNG SLIDING IN IMAGES OF AN ULTRASOUND SCAN

CROSS-REFERENCE TO RELATED APPLICATIONS/INCORPORATION BY REFERENCE

[Not Applicable]

FIELD OF THE INVENTION

Certain embodiments of the invention relate to ultrasound imaging. More specifically, certain embodiments of the invention relate to a method and system for enhanced visualization of lung sliding by automatically detecting and highlighting lung sliding in images of an ultrasound scan.

BACKGROUND OF THE INVENTION

Ultrasound imaging is a medical imaging technique for imaging organs and soft tissues in a human body. Ultrasound imaging uses real time, non-invasive high frequency sound waves to produce a series of two-dimensional (2D) and/or three-dimensional (3D) images.

Pneumothorax, also referred to as collapsed lung, is a common medical condition that is frequently observed in emergency medicine or critical care departments. Pneumothorax may be a spontaneous or secondary condition of chronic obstructive pulmonary disease (COPD), trauma, or a medical procedure. The initial evaluation of trauma patients typically involves a chest X-ray, which has a poor sensitivity for the detection of pneumothorax. Ultrasound has shown to be more sensitive than X-ray for detection of pneumothorax and has the advantage of being non-radiating and immediately available at the critical-care or emergency-room bedside.

Figure 4:
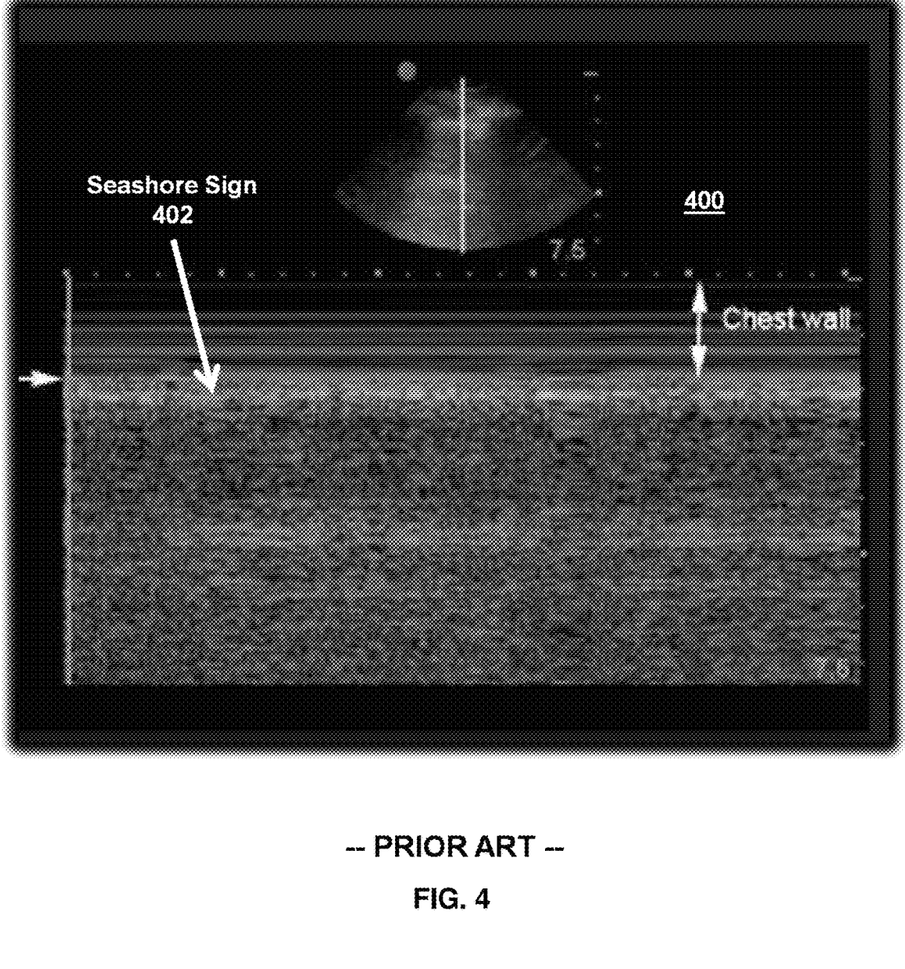
FIG. 4 is a screenshot of an exemplary virtual M mode image having an M mode ultrasound image portion showing a seashore sign as is known in the art.
Figure 5:
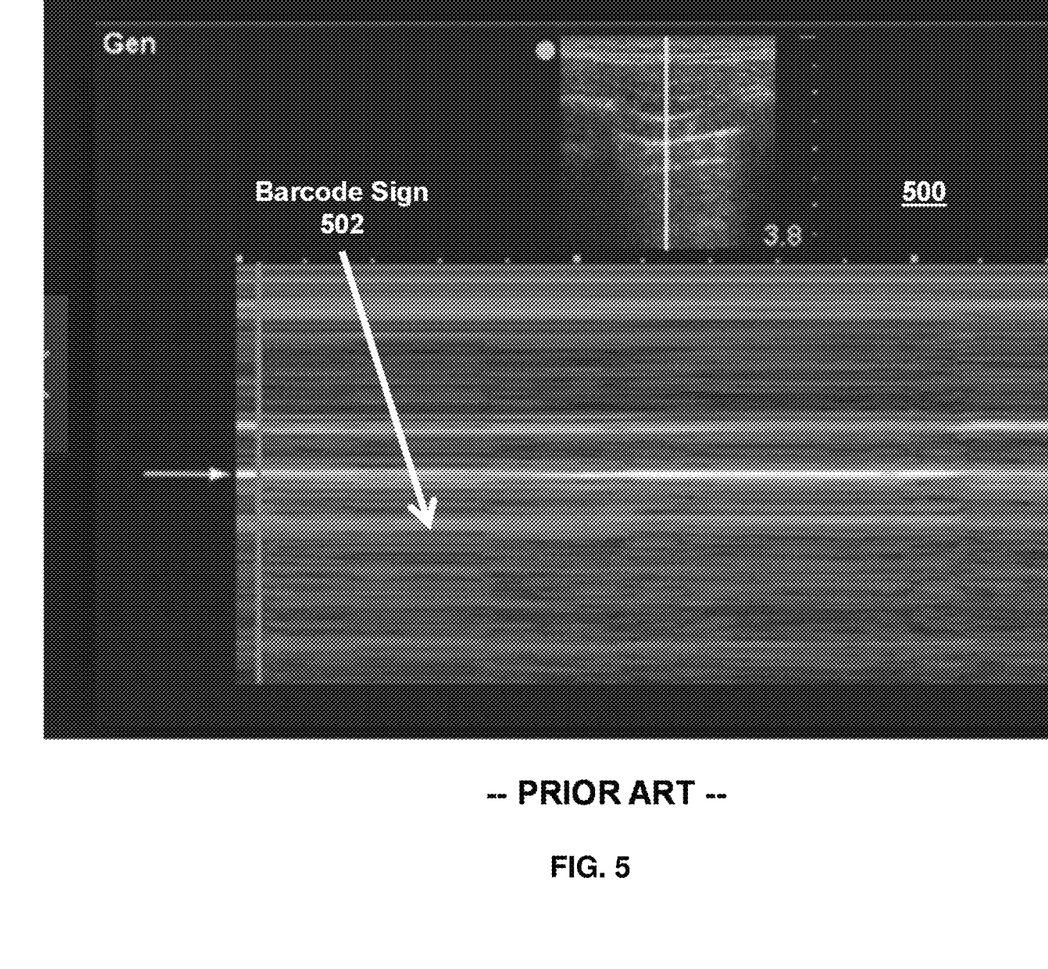
FIG. 5 is a screenshot of an exemplary virtual M mode image having an M mode ultrasound image portion showing a barcode sign as is known in the art.

Ultrasound images may provide various indications useful in identifying pneumothorax. For example, the pleura region of B mode ultrasound images may provide a "shimmering" effect that indicates lung sliding. In M mode images, a normal lung may show a "seashore sign" with transition at the pleura between subcutaneous tissue above the pleura and a wavy pattern of movement generated by lung sliding motion below the pleura. FIG. 4 is a screenshot of an exemplary virtual M mode image 400 having an M mode ultrasound image portion showing a seashore sign 402 as is known in the art. Pneumothorax prevents detection of motion in M mode images, appearing instead as a "barcode sign." FIG. 5 is a screenshot of an exemplary virtual M mode image 500 having an M mode ultrasound image portion showing a barcode sign 502 as is known in the art.

Another indication useful in identifying pneumothorax in ultrasound images includes the absence of B lines, which are comet-tail reverberation artifacts that appear as bright vertical lines extending from the pleura to the bottom of an ultrasound image. Moreover, identification of a lung point or transition point, which is a point on the pleura where a transition between normal lung sliding and no lung sliding can be seen, is indicative of pneumothorax. Lung function is regional in nature. For example, a condition present in one section of one lung may not be present in other sections of the same lung or in the other lung. Moreover, analysis of lung ultrasound images is typically performed on an ultrasound scan covering at least one breathing cycle. Currently, a physician may review and analyze multiple images from multiple zones of the lungs to manually detect indications of pneumothorax. Detecting lung sliding is a labor intensive process when reviewing large numbers of images. Furthermore, detecting the "shimmering" signs in B mode images and/or the "seashore sign" or "barcode sign" in M mode images requires significant effort and can be missed.

Existing ultrasound and post-processing systems do not enhance the visualization of lung sliding for review of an operator of an ultrasound system. Furthermore, existing systems do not automatically identify a representative ultrasound image that highlights potential pneumothorax based on no or partial sliding. Moreover, existing systems do not provide a virtual M mode tool based on raw data of colorized B mode images to facilitate review of M mode image data corresponding with colorized and non-colorized portions from a B mode image display.

Further limitations and disadvantages of conventional and traditional approaches will become apparent to one of skill in the art, through comparison of such systems with some aspects of the present invention as set forth in the remainder of the present application with reference to the drawings.

BRIEF SUMMARY OF THE INVENTION

A system and/or method is provided for enhanced visualization of lung sliding by automatically detecting and highlighting lung sliding in images of an ultrasound scan, substantially as shown in and/or described in connection with at least one of the figures, as set forth more completely in the claims.

These and other advantages, aspects and novel features of the present invention, as well as details of an illustrated embodiment thereof, will be more fully understood from the following description and drawings.

DETAILED DESCRIPTION OF THE INVENTION

Certain embodiments of the invention may be found in a method and system for enhanced visualization of lung sliding by automatically detecting and highlighting lung sliding in images of an ultrasound scan. For example, aspects of the present invention have the technical effect of automatically providing real-time ultrasound images enhanced to identify lung sliding for presentation to an ultrasound operator. Moreover, aspects of the present invention have the technical effect of automatically identifying a representative ultrasound image that highlights potential pneumothorax based on no or partial lung sliding for review by an ultrasound operator. Furthermore, aspects of the present invention have the technical effect of providing tools for positioning one or more virtual M mode lines in a B mode image display portion of a virtual M mode image to select M mode image data for display in at least one M mode image display portion of the virtual M mode image.

The foregoing summary, as well as the following detailed description of certain embodiments will be better understood when read in conjunction with the appended drawings. To the extent that the figures illustrate diagrams of the functional blocks of various embodiments, the functional blocks are not necessarily indicative of the division between hardware circuitry. Thus, for example, one or more of the functional blocks (e.g., processors or memories) may be implemented in a single piece of hardware (e.g., a general purpose signal processor or a block of random access memory, hard disk, or the like) or multiple pieces of hardware. Similarly, the programs may be stand alone programs, may be incorporated as subroutines in an operating system, may be functions in an installed software package, and the like. It should be understood that the various embodiments are not limited to the arrangements and instrumentality shown in the drawings. It should also be understood that the embodiments may be combined, or that other embodiments may be utilized and that structural, logical and electrical changes may be made without departing from the scope of the various embodiments of the present invention. The following detailed description is, therefore, not to be taken in a limiting sense, and the scope of the present invention is defined by the appended claims and their equivalents.

As used herein, an element or step recited in the singular and proceeded with the word "a" or "an" should be understood as not excluding plural of said elements or steps, unless such exclusion is explicitly stated. Furthermore, references to "one embodiment" are not intended to be interpreted as excluding the existence of additional embodiments that also incorporate the recited features. Moreover, unless explicitly stated to the contrary, embodiments "comprising" or "having" an element or a plurality of elements having a particular property may include additional elements not having that property.

Also as used herein, the term "image" broadly refers to both viewable images and data representing a viewable image. However, many embodiments generate (or are configured to generate) at least one viewable image. In addition, as used herein, the phrase "image" is used to refer to an ultrasound mode such as B-mode, CF-mode and/or sub-modes of CF such as TVI, Angio, B-flow, BMI, BMI_Angio, and in some cases also MM, CM, PW, TVD, CW where the "image" and/or "plane" includes a single beam or multiple beams.

Furthermore, the term processor or processing unit, as used herein, refers to any type of processing unit that can carry out the required calculations needed for the invention, such as single or multi-core: CPU, Graphics Board, DSP, FPGA, ASIC or a combination thereof.

It should be noted that various embodiments described herein that generate or form images may include processing for forming images that in some embodiments includes beamforming and in other embodiments does not include beamforming. For example, an image can be formed without beamforming, such as by multiplying the matrix of demodulated data by a matrix of coefficients so that the product is the image, and wherein the process does not form any "beams". Also, forming of images may be performed using channel combinations that may originate from more than one transmit event (e.g., synthetic aperture techniques).

In various embodiments, ultrasound processing to form images is performed, for example, including ultrasound beamforming, such as receive beamforming, in software, firmware, hardware, or a combination thereof. One implementation of an ultrasound system having a software beamformer architecture formed in accordance with various embodiments is illustrated in FIG. 1.

Figure 1:
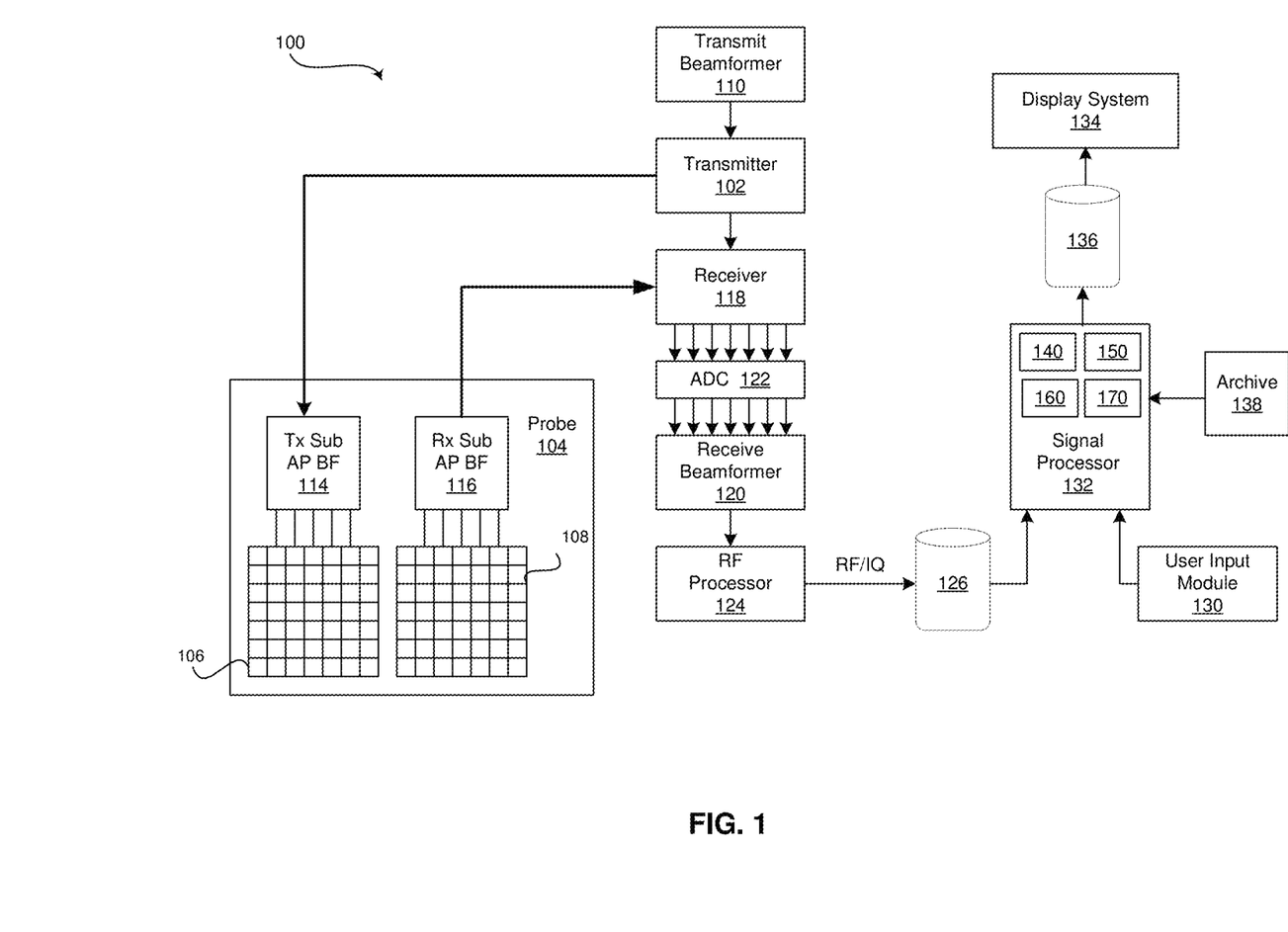
FIG. 1 is a block diagram of an exemplary ultrasound system that is operable to provide enhanced visualization of lung sliding by automatically detecting and highlighting lung sliding in images of an ultrasound scan, in accordance with an embodiment of the invention.

FIG. 1 is a block diagram of an exemplary ultrasound system 100 that is operable to provide enhanced visualization of lung sliding by automatically detecting and highlighting 206 lung sliding in images 200, 300 of an ultrasound scan, in accordance with an embodiment of the invention. Referring to FIG. 1, there is shown an ultrasound system 100 comprising a transmitter 102, an ultrasound probe 104, a transmit beamformer 110, a receiver 118, a receive beamformer 120, a RF processor 124, a RF/IQ buffer 126, a user input module 130, a signal processor 132, an archive 138, an image buffer 136, and a display system 134.

The transmitter 102 may comprise suitable logic, circuitry, interfaces and/or code that may be operable to drive an ultrasound probe 104. The ultrasound probe 104 may comprise a one dimensional (1D, 1.25D, 1.5D or 1.75D) array, two dimensional (2D) array, or three dimensional (3D) array of piezoelectric elements. The ultrasound probe 104 may comprise a group of transmit transducer elements 106 and a group of receive transducer elements 108, that normally constitute the same elements.

The transmit beamformer 110 may comprise suitable logic, circuitry, interfaces and/or code that may be operable to control the transmitter 102 which, through a transmit sub-aperture beamformer 114, drives the group of transmit transducer elements 106 to emit ultrasonic transmit signals into a region of interest (e.g., human, animal, underground cavity, physical structure, and the like). The transmitted ultrasonic signals 107 may be back-scattered from structures in the object of interest, like blood cells or tissue, to produce echoes. The echoes are received by the receive transducer elements 108. The group of receive transducer elements 108 in the ultrasound probe 104 may be operable to convert the received echoes into analog signals, undergo sub-aperture beamforming by a receive sub-aperture beamformer 116, and are then communicated to a receiver 118.

The receiver 118 may comprise suitable logic, circuitry, interfaces and/or code that may be operable to receive and demodulate the signals from the receive sub-aperture beamformer 116. The demodulated analog signals may be communicated to one or more of the plurality of A/D converters 122. The plurality of A/D converters 122 may comprise suitable logic, circuitry, interfaces and/or code that may be operable to convert the demodulated analog signals from the receiver 118 to corresponding digital signals. The plurality of A/D converters 122 are disposed between the receiver 118 and the receive beamformer 120. Notwithstanding, the invention is not limited in this regard. Accordingly, in some embodiments of the invention, the plurality of A/D converters 122 may be integrated within the receiver 118.

The receive beamformer 120 may comprise suitable logic, circuitry, interfaces and/or code that may be operable to perform digital beamforming processing on the signals received from the plurality of A/D converters 122. The resulting processed information may be converted back to corresponding RF signals. The corresponding output RF signals that are output from the receive beamformer 120 may be communicated to the RF processor 124. In accordance with some embodiments of the invention, the receiver 118, the plurality of A/D converters 122, and the beamformer 120 may be integrated into a single beamformer, which may be digital.

The RF processor 124 may comprise suitable logic, circuitry, interfaces and/or code that may be operable to demodulate the RF signals. In accordance with an embodiment of the invention, the RF processor 124 may comprise a complex demodulator (not shown) that is operable to demodulate the RF signals to form I/Q data pairs that are representative of the corresponding echo signals. The RF or I/Q signal data may then be communicated to an RF/IQ buffer 126. The RF/IQ buffer 126 may comprise suitable logic, circuitry, interfaces and/or code that may be operable to provide temporary storage of the RF or I/Q signal data, which is generated by the RF processor 124.

The user input module 130 may be utilized to input patient data, image acquisition and scan parameters, settings, configuration parameters, change scan mode, manipulate tools for reviewing acquired ultrasound data, and the like. In an exemplary embodiment of the invention, the user input module 130 may be operable to configure, manage and/or control operation of one or more components and/or modules in the ultrasound system 100. In this regard, the user input module 130 may be operable to configure, manage and/or control operation of transmitter 102, the ultrasound probe 104, the transmit beamformer 110, the receiver 118, the receive beamformer 120, the RF processor 124, the RF/IQ buffer 126, the user input module 130, the signal processor 132, the image buffer 136, the archive 138, and/or the display system 134.

Figure 3:
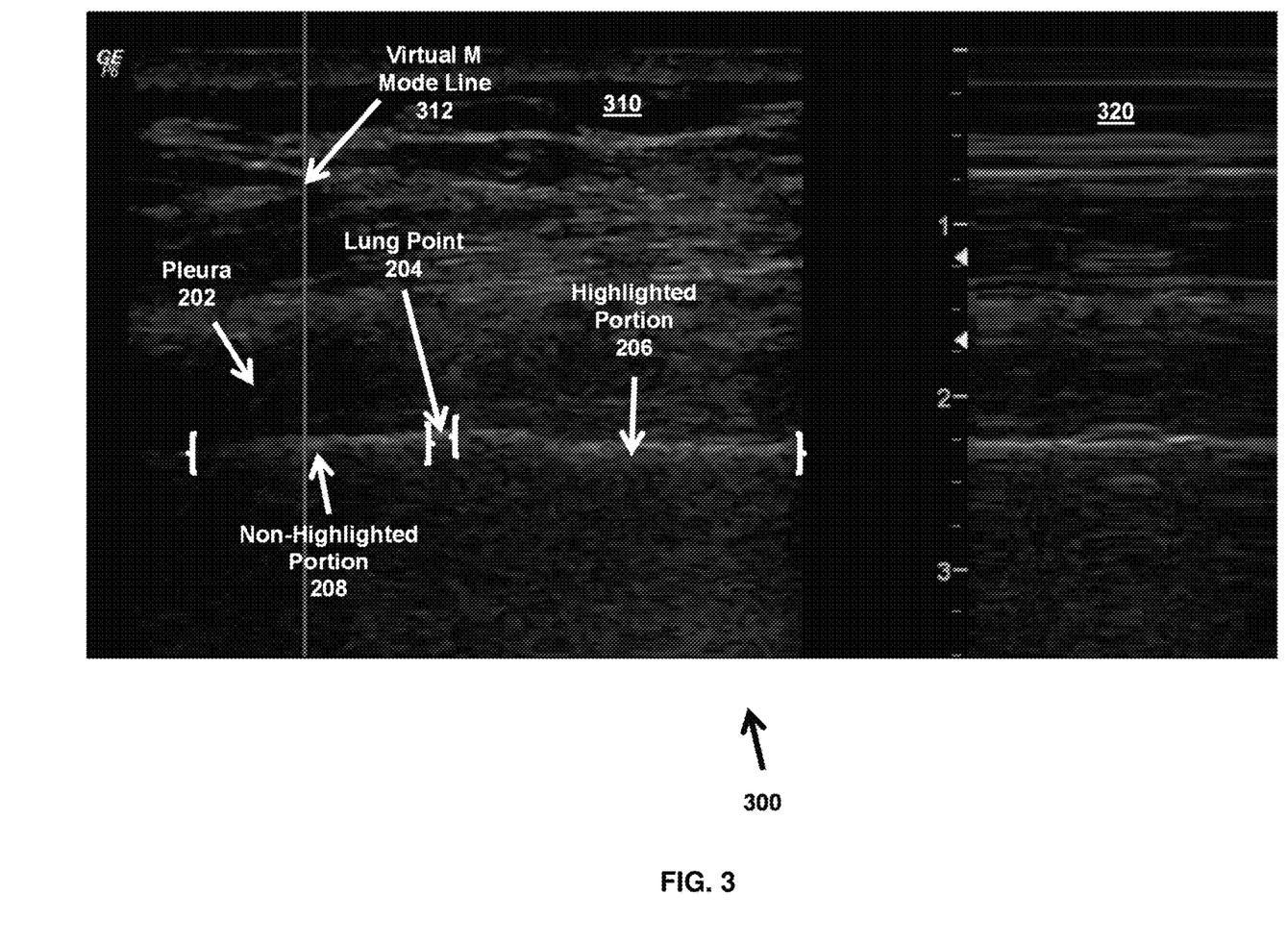
FIG. 3 is a screenshot of an exemplary enhanced virtual M mode ultrasound image having an enhanced B mode image display portion comprising a virtual M mode line and an M mode image display portion corresponding with the virtual M mode line, in accordance with an embodiment of the invention.

In various embodiments, the user input module 130 may be operable to manipulate tools for reviewing acquired ultrasound data. FIG. 3 is a screenshot of an exemplary enhanced virtual M mode ultrasound image 300 having an enhanced B mode image display portion 310 comprising a virtual M mode line 312 and an M mode image display portion 320 corresponding with the virtual M mode line 312, in accordance with an embodiment of the invention. Referring to FIG. 3 and as described in detail below, a user input module 130 may be operable to control the positioning of the virtual M mode line 312 in the virtual M mode image 300 to select the M mode image data to display in the M mode image display portion 320. The user input module 130 can be a mousing device, trackball, keyboard, touch screen display, remote control, button, switch, sliding bar, voice activated input, or any suitable device or mechanism operable to receive a user input. The user input module 130 may be integrated with other components, such as the ultrasound probe 104 or display system 134, or can be a separate component.

The signal processor 132 may comprise suitable logic, circuitry, interfaces and/or code that may be operable to process the ultrasound scan data for generating an ultrasound image for presentation on a display system 134. The signal processor 132 is operable to perform one or more processing operations according to a plurality of selectable ultrasound modalities on the acquired ultrasound scan data. Acquired ultrasound scan data may be processed in real-time during a scanning session as the echo signals are received. Additionally or alternatively, the ultrasound scan data may be stored temporarily in the RF/IQ buffer 126 during a scanning session and processed in less than real-time in a live or off-line operation. In the exemplary embodiment, the signal processor 132 may comprise a detection module 140, a lung sliding processing module 150, a representative frame selection module 160, and an examination analysis module 170.

The ultrasound system 100 may be operable to continuously acquire ultrasound information at a frame rate that is suitable for the imaging situation in question. Typical frame rates range from 20-70 but may be lower or higher. The acquired ultrasound information may be displayed on the display system 134 at a display-rate that can be the same as the frame rate, or slower or faster. An image buffer 136 is included for storing processed frames of acquired ultrasound information that are not scheduled to be displayed immediately. Preferably, the image buffer 136 is of sufficient capacity to store at least several seconds worth of frames of ultrasound information. The frames of ultrasound information are stored in a manner to facilitate retrieval thereof according to its order or time of acquisition. The image buffer 136 may be embodied as any known data storage medium.

Figure 2:
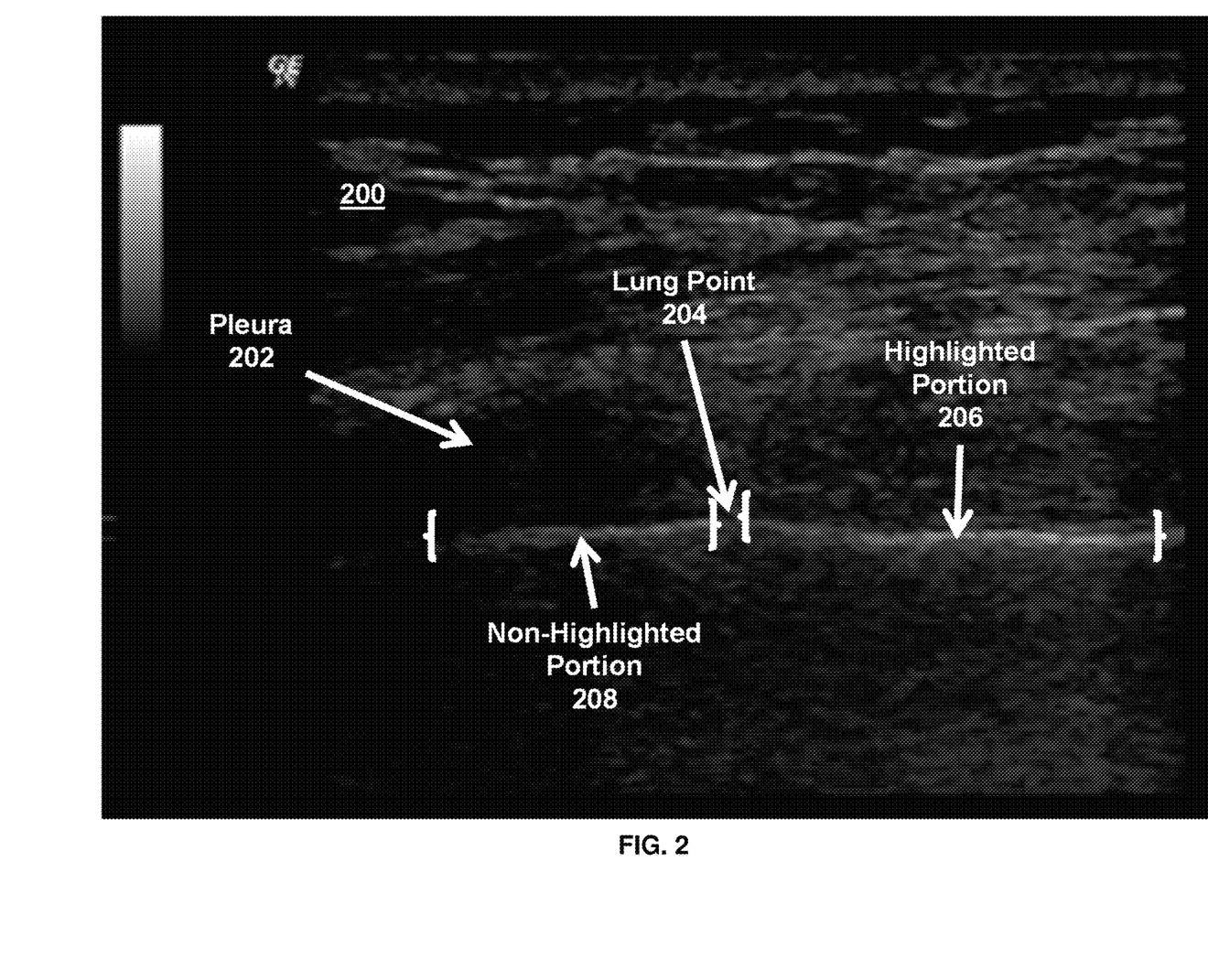
FIG. 2 is a screenshot of an exemplary enhanced B mode ultrasound image of a portion of a lung having a highlighted portion identifying lung sliding, in accordance with an embodiment of the invention.

The detection module 140 may comprise suitable logic, circuitry, interfaces and/or code that may be operable to determine whether an ultrasound probe is moving, identify a pleura 202 in each image 200, 300 of an acquired ultrasound scan video clip, and analyze the pleura 202 and surrounding region to detect signs of lung sliding in each image 200, 300 of the acquired video clip. FIG. 2 is a screenshot of an exemplary enhanced B mode ultrasound image 200 of a portion of a lung having a highlighted portion 206 identifying lung sliding, in accordance with an embodiment of the invention. Referring to FIG. 2, an ultrasound image 200 of a lung is shown having a pleura line 202 extending generally horizontal. The detection module 140 may search the image data 200 for the bright horizontal section that identifies the pleura 202. In an exemplary embodiment, the pleura 202 may be identified based at least in part on a location of detected ribs (not shown), which may be recognized by their acoustic shadow.

The detection module 140 may analyze each pixel at the pleura and a region surrounding the pleura in each image of an acquired ultrasound video clip to detect signs of lung sliding. For example, the detection module 140 may automatically position a colorizing analysis box of a predefined size and shape over the image 200 based on the detected position of the pleura 202 and/or ribs. The detection module 140 may analyze the pixels within the positioned colorizing analysis box. The detection can be done by horizontal cross correlation between consecutive images, by temporal derivative of the pixels in that region, or any suitable image detection techniques.

The detection module 140 may receive feedback from the ultrasound probe 104 and/or apply image detection and analysis techniques or algorithms to analyze the image data to check for probe 104 motion. For example, the detection module 140 may analyze changes to the superficial portion of the image above the pleura 202 using cross correlation or any suitable image detection technique. If the detection module 140 of the signal processor 132 detects that the probe 104 is moving, the detection module 140 may suspend highlighting of lung sliding in the ultrasound images 200, 300 applied by the lung sliding processing module 150 as described below.

The lung sliding processing module 150 may comprise suitable logic, circuitry, interfaces and/or code that may be operable to highlight the portions of the pleura 202 and surrounding region where lung sliding is detected in each image 200, 300 of the ultrasound video clip. The highlighting may be performed by colorizing the ultrasound pixels representing the lung sliding in the images 200, 300, superimposing a marker on the images 200, 300, and/or any suitable manner for drawing attention to detected lung sliding for presentation to an operator and/or physician reviewing the images 200, 300 at the display system 134. In various embodiments, the highlighting by the lung sliding processing module 150 may be performed dynamically such that the images 200, 300 may be displayed at the display system 134 in substantially real-time.

Referring to FIG. 2, a screenshot of an exemplary enhanced B mode ultrasound image 200 of a portion of a lung having a highlighted portion 206 identifying lung sliding is shown. The B mode ultrasound image 200 illustrates a pleura 202 of a lung having a highlighted portion 206, a non-highlighted portion 208, and a lung point 204. The pleura 202 is the bright horizontal line extending generally horizontal across the B mode image 200. The highlighted portion 206 corresponds with a portion of the pleura 202 that has exhibited signs of lung sliding as detected by the detection module 140. The highlighted portion 206 may comprise colorized pixels provided by the lung sliding processing module 150 to enhance visualization of the lung sliding for an operator viewing the B mode ultrasound image 200 at a display system 134. The non-highlighted portion 208 corresponds with a portion of the pleura 202 that has not shown signs of lung sliding based on the analysis performed by the detection module 140. The lung point 204 is the portion of the pleura 202 where the lung sliding portion 206 meets the portion of the pleura not exhibiting lung sliding 208.

FIG. 3 is a screenshot of an exemplary enhanced virtual M mode ultrasound image 300 having an enhanced B mode image display portion 310 comprising a virtual M mode line 312 and an M mode image display portion 320 corresponding with the virtual M mode line 312, in accordance with an embodiment of the invention. Referring to FIG. 3, the virtual M mode ultrasound image 300 comprises an enhanced B mode image display portion 310 and an M mode image display portion 320. The enhanced B mode image display portion 310 may share various characteristics, for example, with the B mode ultrasound image 200 of FIG. 2. As an example, the enhanced B mode image display portion 310 may illustrate a pleura 202 of a lung having a highlighted portion 206, a non-highlighted portion 208, and a lung point 204. The highlighted portion 206 may be, for example, colorization added by the lung processing module 150 to pixels exhibiting lung sliding as identified by the detection module 140.

In various embodiments, the ultrasound images 200, 300 having the highlighting 206 identifying the lung sliding may be dynamically presented at a display system 134 such that an operator of the ultrasound probe 104 may view the highlighted images 200, 300 in substantially real-time. The images 200, 300 highlighted by the lung sliding processing module 150 may be stored at the archive 138. The archive 138 may be a local archive, a Picture Archiving and Communication System (PACS), or any suitable device for storing ultrasound images and related information.

The representative frame selection module 160 may comprise suitable logic, circuitry, interfaces and/or code that may be operable to review each image 200, 300 of an ultrasound video clip and automatically select the image 200, 300 that shows potential pneumothorax based on no or partial sliding. For example, the representative frame selection module 160 may automatically select and present a representative image 200, 300 at a display system 134. In various embodiments, the representative frame selection module 160 may automatically select the frame 200, 300 of the video clip having a lung point 204, a highlighted portion 206, and a non-highlighted portion 208. In image sets having a lung point 204, priority may be given to an image with a lung point 204 located at the center of the image 200, 300. Additionally or alternatively, the representative frame selection module 160 may select an image 200, 300 where the pleura 202 is completely non-highlighted 208 indicating no lung sliding if an image 200, 300 having a lung point 204 is not available. In certain embodiments, a physician reviewing the ultrasound images 200, 300 may review each of the images to manually select a representative image 200, 300. In various embodiments, a representative image 200, 300 may be stored in the archive 138, such as a local archive or a PACS, for each imaged zone of a lung.

The examination analysis module 170 may comprise suitable logic, circuitry, interfaces and/or code that may be operable to present ultrasound examination images 200, 300 and tools for analyzing examination images at the display system 134. For example, the examination analysis module 170 may present an enhanced virtual M mode ultrasound image 300 having a virtual M mode line tool 312 for selecting M mode image data for display. Referring to FIG. 3, a screenshot of an exemplary enhanced virtual M mode ultrasound image 300 having an enhanced B mode image display portion 310 comprising a virtual M mode line 312 and an M mode image display portion 320 corresponding with the virtual M mode line 312 is shown. The enhanced B mode image display portion 310 may share various characteristics with, for example, the B mode ultrasound image 200 of FIG. 2. As an example, the enhanced B mode image display portion 310 may illustrate a pleura 202 of a lung having a highlighted portion 206, a non-highlighted portion 208, and a lung point 204. The highlighted portion 206 may be, for example, colorization added by the lung processing module 150 to pixels exhibiting lung sliding as identified by the detection module 140. The virtual M mode line tool 312 allows a user to select the M mode image data for display in the M mode image display portion 320 of the enhanced virtual M mode ultrasound image 300.

For example, by positioning the virtual M mode line tool 312 with the user input module 130, such as a mousing device or a trackball, a user may visualize M mode data 320 corresponding with a highlighted portion 206 that is representative of lung sliding. Specifically, the user may visualize M mode ultrasound data 320 appearing as a seashore sign commonly associated with lung sliding when the virtual M mode line 312 is positioned in the highlighted portion 206 of the enhanced B mode image display portion 310. FIG. 4 is a screenshot of an exemplary virtual M mode image 400 having an M mode ultrasound image portion showing a seashore sign 402 as is known in the art.

As another example, by positioning the virtual M mode line tool 312 with the user input module 130, a user may visualize M mode data 320 corresponding with a non-highlighted portion 208 that is representative of no lung sliding. Specifically, the user may visualize M mode ultrasound data 320 appearing as a barcode sign commonly associated with no lung sliding when the virtual M mode line 312 is positioned in the non-highlighted portion 208 of the enhanced B mode image display portion 310. FIG. 5 is a screenshot of an exemplary virtual M mode image 500 having an M mode ultrasound image portion showing a barcode sign 502 as is known in the art.

In various embodiments, the enhanced virtual M mode ultrasound image 300 may include multiple virtual M mode lines 312, each of the virtual M mode lines having a corresponding M mode image display portion 320. For example, a first virtual M mode line 312 may be positioned over a highlighted portion 206 of the B mode image display portion 310 and a second virtual mode line 312 may be positioned over a non-highlighted portion 208 of the B mode image display portion 310. In the above example, the enhanced virtual M mode ultrasound image 300 may include two M mode image display portions 320, each corresponding with one of the virtual M mode lines 312. In certain embodiments, the examination analysis module 170 may automatically position one or more virtual M mode lines 312. For example, the examination analysis module 170 may automatically position a first virtual M mode line 312 in a highlighted portion 206 and a second virtual M mode line 312 in a non-highlighted portion 208 of the B mode image display portion 310. The enhanced virtual M mode ultrasound image 300 may be stored in an archive 138, such as a local archive, PACS, or any suitable storage device. The enhanced virtual M mode ultrasound image 300 may be displayed at the display system 134 of the ultrasound system 100 or any suitable display component including remote display components.

Figure 6:
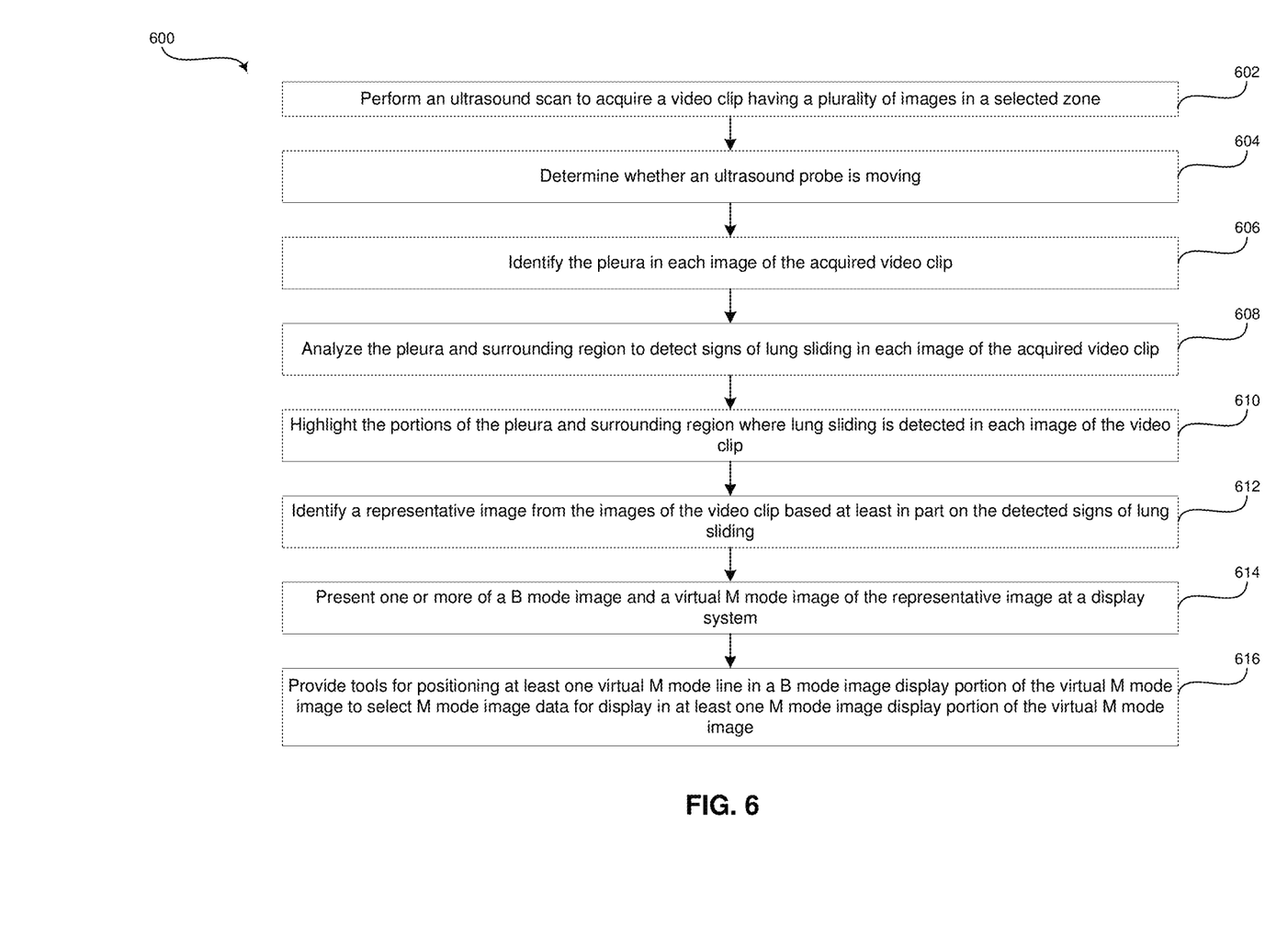
FIG. 6 is a flow chart illustrating exemplary steps that may be utilized for providing enhanced visualization of lung sliding by automatically detecting and highlighting lung sliding in images of an ultrasound scan, in accordance with an embodiment of the invention.

FIG. 6 is a flow chart 600 illustrating exemplary steps 602-616 that may be utilized for providing enhanced visualization of lung sliding by automatically detecting and highlighting 206 lung sliding in images 200, 300 of an ultrasound scan, in accordance with an embodiment of the invention. Referring to FIG. 6, there is shown a flow chart 600 comprising exemplary steps 602 through 616. Certain embodiments of the present invention may omit one or more of the steps, and/or perform the steps in a different order than the order listed, and/or combine certain of the steps discussed below. For example, some steps may not be performed in certain embodiments of the present invention. As a further example, certain steps may be performed in a different temporal order, including simultaneously, than listed below.

At step 602, the ultrasound probe 104 in the ultrasound system 100 may be operable to perform an ultrasound scan of a zone of the lung. For example, an ultrasound operator may select a layout of the lung having a plurality of zones, such as two columns and two rows for each lung or two columns and three rows for each lung. The operator may acquire an ultrasound video clip having a plurality of frames for each of the zones of the lungs. The ultrasound scan may be acquired, for example, over the duration of at least one breathing cycle. The breathing cycle can be detected automatically, by a specified duration, or by an operator, among other things. For example, if a patient is using a ventilator, the ventilator can provide a signal to the signal processor 132 identifying the breathing cycle duration. As another example, the breathing cycle may be defined by an operator input at a user input module 130 or be a default value, such as 3-5 seconds. Further, an operator may identify the end of a breathing cycle by providing an input at the user input module 130, such as by pressing a button on the ultrasound probe 104.

At step 604, the detection module 140 of the signal processor 132 may determine whether the ultrasound probe 104 is moving. For example, the detection module 140 may receive feedback from the ultrasound probe 104 and/or apply image detection and analysis techniques or algorithms to analyze the image data to check for probe 104 motion. In an exemplary embodiment, the detection module 140 may analyze changes to the superficial portion of the image above the pleura 202 using cross correlation or any suitable image detection technique. If the detection module 140 of the signal processor 132 detects that the probe 104 is moving, the detection module 140 may suspend highlighting of lung sliding in the ultrasound images 200, 300 applied by the lung sliding processing module 150 at step 610 below.

At step 606, the detection module 140 of the signal processor 132 may identify the pleura 202 in each image 200, 300 of the acquired video clip. For example, the detection module 150 may apply image detection techniques and/or algorithms to automatically search the image data for the bright horizontal section that identifies the pleura 202. In an exemplary embodiment, the pleura 202 may be identified based at least in part on the location of ribs, which may be identified by superficial hyper-echoic structures with dark shadows that extend to the bottom of the image 200, 300.

At step 608, the detection module 140 of the signal processor 132 may analyze the pleura 202 and surrounding region in each image 200, 300 of the acquired video clip to detect lung sliding. For example, the detection module 140 may automatically position a colorizing analysis box of a predefined size and shape on the image based on the position of the pleura 202 as detected at step 606. The detection module 140 may analyze each of the pixels within the positioned colorizing analysis box by applying image detection and analysis algorithms, such as horizontal cross correlation between consecutive images, computing the temporal derivative of the pixels in that region, or any suitable image detection techniques.

At step 610, the lung sliding processing module 150 of the signal processor 132 may highlight 206 the detected lung sliding on each image 200, 300 of the video clip. For example, the lung sliding processing module 150 may highlight 206 the detected lung sliding by superimposing a marker on the image 200, 300, colorizing the ultrasound pixels representing the lung sliding in the image 200, 300, and/or any suitable manner for drawing attention to detected lung sliding for presentation to an operator and/or physician reviewing the image 200, 300. In various embodiments, the ultrasound images 200, 300 having the highlighting 206 identifying the lung sliding may be dynamically presented at a display system 134 such that an operator of the ultrasound probe 104 may view the highlighted images 200, 300 in substantially real-time. In certain embodiments, the lung processing module 150 suspends highlighting 206 of ultrasound images 200, 300 if the detection module 140 indicates that the ultrasound probe 104 is moving.

At step 612, the representative frame selection module 160 of the signal processor 132 may identify a representative image 200, 300 from the images of the video clip based at least in part on the detected signs of lung sliding. For example, the representative frame selection module 160 may be operable to review each image 200, 300 of a video clip and automatically select the image 200, 300 that identifies potential pneumothorax based on no or partial lung sliding. Specifically, the representative frame selection module 160 may be operable to automatically select the image 200, 300 having a lung point 204. The representative frame selection module 160 may select the image 200, 300 having a lung point 204 centered in the image 200, 300 if more than one image 200, 300 has a lung point 204. If none of the reviewed images has a lung point 204, the representative frame selection module 160 may be operable to automatically select an image 200, 300 that is completely non-highlighted 208, which is representative of no lung sliding and potentially identifies pneumothorax. The images 200, 300 that are fully highlighted 206 indicate lung sliding presence, which rules out pneumothorax at that location. The representative image 200, 300 selected by the representative frame selection module 160 may be stored in an archive 138, such as a local archive, PACS, or any suitable storage medium.

At step 614, the examination analysis module 170 of the signal processor 132 may present a B mode image 200 and/or a virtual M mode image 300 of the representative image at a display system 134. For example, the examination analysis module 170 may present a B mode image 200 as illustrated in FIG. 2, having portions that exhibit lung sliding being highlighted 206 and/or portions that do not exhibit lung sliding being non-highlighted 208. As another example, the examination analysis module 170 may present an enhanced virtual M mode ultrasound image 300 having a B mode image display portion 310 and an M mode image display portion 320. The M mode image data displayed in the M mode image display portion 320 corresponds with a virtual M mode line 312 position in the B mode image display portion 310. The B mode image display portion 310 may share various characteristics with the B mode image 200 of FIG. 2. For example, the B mode image display portion 310 may have portions exhibiting lung sliding being highlighted 206 and/or portions that do not exhibit lung sliding being non-highlighted 208. The representative image 200, 300 may be retrieved from an archive 138, such as a local archive, PACS, or any suitable storage device, for presentation at the display system 134 of the ultrasound system 100 or any suitable display component including remote display components.

At step 616, the examination analysis module 170 of the signal processor 132 may be operable to present tools for analyzing examination images at the display system 134. For example, the examination analysis module 170 may be operable to display an enhanced virtual M mode ultrasound image 300 having an enhanced B mode image display portion 310 comprising a virtual M mode line 312 and an M mode image display portion 320 corresponding with the virtual M mode line 312. The virtual M mode line tool 312 may be operable to allow a user to select the M mode image data for display in the M mode image display portion 320 of the enhanced virtual M mode ultrasound image 300. For example, a user may visualize M mode data 320 corresponding with a highlighted portion 206 that is representative of lung sliding by positioning the virtual M mode line tool 312 over the highlighted portion 206 in the B mode image display portion 310. As another example, a user may visualize M mode data 320 corresponding with a non-highlighted portion 208 that is representative of no lung sliding by positioning the virtual M mode line tool 312 over the non-highlighted portion 208 in the B mode image display portion 310.

The virtual M mode line 312 may be positioned automatically by the examination analysis module 170 and/or with the user input module 130, such as a mousing device or a trackball, among other things. In various embodiments, the enhanced virtual M mode ultrasound image 300 may include multiple virtual M mode lines 312, each of the virtual M mode lines having a corresponding M mode image display portion 320. For example, a first virtual M mode line 312 may be positioned over a highlighted portion 206 of the B mode image display portion 310 and a second virtual mode line 312 may be positioned over a non-highlighted portion 208 of the B mode image display portion 310. In the above example, the enhanced virtual M mode ultrasound image 300 may include two M mode image display portions 320, each corresponding with one of the virtual M mode lines 312. In certain embodiments, the examination analysis module 170 may automatically position one or more virtual M mode lines 312. For example, the examination analysis module 170 may automatically position a first virtual M mode line 312 in a highlighted portion 206 and a second virtual M mode line 312 in a non-highlighted portion 208 of the B mode image display portion 310.

Aspects of the present invention provide a method 600 and system 100 for providing enhanced visualization of lung sliding by automatically detecting and highlighting 206 lung sliding in images 200, 300 of an ultrasound scan. In accordance with various embodiments of the invention, the method 600 comprises performing 602, by an ultrasound probe 104 of an ultrasound system 100, an ultrasound scan to acquire a video clip having a plurality of images 200, 300 of at least a portion of a lung. The method 600 comprises detecting 608, by a processor 132, 140 of the ultrasound system 100, lung sliding in each of the plurality of images 200, 300 of the video clip. The method 600 comprises highlighting 610, by the processor 132, 150, the detected lung sliding in each of the plurality of images 200, 300 of the video clip to generate a processed plurality of images. The method 600 comprises displaying 614, by a display system 134 of the ultrasound system 100, at least one of the processed plurality of images as one or more of an enhanced virtual M mode image 300 and an enhanced B mode image 200.

In certain embodiments, the at least one of the processed plurality of images is displayed as the enhanced virtual M mode image 300 having a B mode image display portion 310 and at least one M mode image display portion 320. The B mode image display portion 310 comprises at least one virtual M mode line 312 having a location in the B mode image display portion 310 that corresponds with M mode image data displayed in the at least one M mode image display portion 320. The method 600 comprises positioning 616 the at least one virtual M mode line 312 in the B mode image display portion 310 of the enhanced virtual M mode image 300. The at least one virtual M mode line 312 may be positioned at a highlighted portion 206 of the at least one of the processed plurality of images presented in the B mode image display portion 310 and/or at a non-highlighted portion 208 of the at least one of the processed plurality of images presented in the B mode image display portion 310.

In a representative embodiment, the at least one virtual M mode line 312 in the B mode image display portion 310 of the enhanced virtual M mode image 300 comprises two virtual M mode lines 312. The at least one M mode image display portion 320 of the enhanced virtual M mode image 300 comprises two M mode image display portions 320. A first of the two virtual M mode lines 312 is positioned in the highlighted portion 206 of the at least one of the processed plurality of images presented in the B mode image display portion 310. First M mode image data corresponding with the location of the first of the two virtual M mode lines 312 is displayed at a first of the two M mode image display portions 320. A second of the two virtual M mode lines 312 is positioned in the non-highlighted portion 208 of the at least one of the processed plurality of images presented in the B mode image display portion 310. Second M mode image data corresponding with the location of the second of the two virtual M mode lines 312 is displayed at a second of the two M mode image display portions 320.

In various embodiments, the positioning of the at least one virtual M mode line 312 is performed automatically by the processor 132, 170. In certain embodiments, the positioning of the at least one virtual M mode line 312 is performed in response to a user instruction received at a user interface device 130. In a representative embodiment, the method 600 comprises detecting 606, by the processor 132, 140, a pleura 202 in each of the plurality of images 200, 300 of the video clip. The detecting 608 lung sliding is performed by analyzing pixels of each of the plurality of images 200, 300 of the video clip that are at one or more of the detected pleura 202 and a region surrounding the detected pleura 202.

In certain embodiments, the method 600 comprises detecting 606, by the processor 132, 140, a pleura 202 in each of the plurality of images 200, 300 of the video clip. The method 600 comprises positioning 608, by the processor 132, 140, a colorizing analysis box of a predefined size and shape over each of the plurality of images 200, 300 of the video clip based on the detected location of the pleura 202 in each of the plurality of images 200, 300. In a representative embodiment, the detecting 608 lung sliding is performed by analyzing pixels of each of the plurality of images 200, 300 of the video clip that are within the positioned colorizing analysis box. In various embodiments, the analyzing 608 pixels is performed by one or more of horizontal cross correlation between consecutive images in the plurality of images 200, 300 of the video clip, and computing the temporal derivative of the pixels.

In a representative embodiment, the highlighting 610 in each of the plurality of images 200, 300 of the video clip comprises colorizing pixels of the detected lung sliding. In various embodiments, the method 600 comprises detecting 604, by the processor 132, 140, movement of the ultrasound probe 104. The highlighting 610 the detected lung sliding is not performed in images of the plurality of images 200, 300 of the video clip acquired during detected movement of the ultrasound probe 104. In certain embodiments, the method 600 comprises automatically selecting 612, by the processor 132, 160, the at least one of the processed plurality of images 200, 300 to display by the display system 134 as the one or more of the enhanced B mode image 200 and the enhanced virtual M mode image 300. The automatic selection 612 of the at least one of the processed plurality of images 200, 300 to display is based on a detected lung point 204 in the processed plurality of images 200, 300, a location of the detected lung point 204 in the processed plurality of images 200, 300, and/or a presence of a non-highlighted portion 208 in the processed plurality of images 200, 300. The method 600 comprises storing the automatically selected at least one of the processed plurality of images 200, 300 in an archive 138.

Various embodiments provide a system comprising an ultrasound device 100 that includes an ultrasound probe 104, a processor 132, and a display system 134. The ultrasound probe 104 is operable to perform an ultrasound scan to acquire a video clip having a plurality of images 200, 300 of at least a portion of a lung. The processor 132, 140 may be operable to detect lung sliding in each of the plurality of images 200, 300 of the video clip. The processor 132, 150 may be operable to highlight 206 the detected lung sliding in each of the plurality of images 200, 300 of the video clip to generate a processed plurality of images 200, 300. The display system 134 may be operable to display at least one of the processed plurality of images as one or more of an enhanced B mode image 200 and an enhanced virtual M mode image 300.

In a representative embodiment, the display system 134 may be operable to display the at least one of the processed plurality of images as the enhanced virtual M mode image 300 having the B mode image display portion 310 and at least one M mode image display portion 320. The B mode image display portion 310 comprises the at least one virtual M mode line 312 having a location in the B mode image display portion 310 that corresponds with M mode image data displayed in the at least one M mode image display portion 320. The processor 132, 170 may be operable to position the at least one virtual M mode line 312 in the B mode image display portion 310 of the enhanced virtual M mode image 300. The at least one virtual M mode line 312 may be positioned at a highlighted portion 206 of the at least one of the processed plurality of images presented in the B mode image display portion 310 and/or at a non-highlighted portion 208 of the at least one of the processed plurality of images presented in the B mode image display portion 310.

In certain embodiments, the processor 132, 140 is operable to detect a pleura 202 in each of the plurality of images 200, 300 of the video clip. The processor 132, 140 is operable to detect lung sliding by analyzing pixels of each of the plurality of images 200, 300 of the video clip that are at one or more of the detected pleura 202 and a region surrounding the detected pleura 202. The processor 132, 140 is operable to analyze the pixels by one or more of horizontal cross correlation between consecutive images in the plurality of images 200, 300 of the video clip and computing the temporal derivative of the pixels. In various embodiments, the processor 132, 150 is operable to highlight the detected lung sliding in each of the plurality of images of the video clip by colorizing pixels of the detected lung sliding. In certain embodiments, the processor 132, 140 is operable to detect movement of the ultrasound probe 104. The processor 132, 150 does not highlight the detected lung sliding in images of the plurality of images 200, 300 of the video clip acquired during detected movement of the ultrasound probe 104.

In a representative embodiment, the system comprises an archive 138. The processor 132, 160 is operable to automatically select the at least one of the processed plurality of images 200, 300 to store in the archive 138 and display by the display system 134 as the one or more of the enhanced B mode image 200 and the enhanced virtual M mode image 300. The automatic selection of the at least one of the processed plurality of images 200, 300 to display is based on a detected lung point 204 in the processed plurality of images 200, 300, a location of the detected lung point 204 in the processed plurality of images 200, 300, and/or a presence of a non-highlighted portion 208 in the processed plurality of images 200, 300.

Certain embodiments provide a non-transitory computer readable medium having a stored thereon, a computer program having at least one code section that is executable by a machine for causing the machine to perform steps 600 disclosed herein. Exemplary steps 600 may comprise detecting 608 lung sliding in each of a plurality of images 200, 300 of a video clip by an ultrasound scan. The steps 600 may comprise highlighting 610 the detected lung sliding in each of the plurality of images 200, 300 of the video clip to generate a processed plurality of images 200, 300. The steps 600 may comprise displaying 614 at least one of the processed plurality of images 200, 300 as one or more of an enhanced B mode image 200 and an enhanced M mode image 300.

In various embodiments, the at least one of the processed plurality of images 200, 300 is displayed as an enhanced virtual M mode image 300 having a B mode image display portion 310 and at least one M mode image display portion 320. The B mode image display portion 310 comprises at least one virtual M mode line 312 having a location in the B mode image display portion 310 that corresponds with M mode image data displayed in the at least one M mode image display portion 320. The steps 600 may comprise positioning 616 the at least one virtual M mode line 312 in the B mode image display portion 310 of the enhanced virtual M mode image 300. The at least one virtual M mode line 312 may be position at a highlighted portion 206 of the at least one of the processed plurality of images presented in the B mode image display portion 310 and/or at a non-highlighted portion 208 of the at least one of the processed plurality of images presented in the B mode image display portion 310.

As utilized herein the term "circuitry" refers to physical electronic components (i.e. hardware) and any software and/or firmware ("code") which may configure the hardware, be executed by the hardware, and or otherwise be associated with the hardware. As used herein, for example, a particular processor and memory may comprise a first "circuit" when executing a first one or more lines of code and may comprise a second "circuit" when executing a second one or more lines of code. As utilized herein, "and/or" means any one or more of the items in the list joined by "and/or". As an example, "x and/or y" means any element of the three-element set {(x), (y), (x, y)}. As another example, "x, y, and/or z" means any element of the seven-element set {(x), (y), (z), (x, y), (x, z), (y, z), (x, y, z)}. As utilized herein, the term "exemplary" means serving as a non-limiting example, instance, or illustration. As utilized herein, the terms "e.g.," and "for example" set off lists of one or more non-limiting examples, instances, or illustrations. As utilized herein, circuitry is "operable" to perform a function whenever the circuitry comprises the necessary hardware and code (if any is necessary) to perform the function, regardless of whether performance of the function is disabled, or not enabled, by some user-configurable setting.

Other embodiments of the invention may provide a computer readable device and/or a non-transitory computer readable medium, and/or a machine readable device and/or a non-transitory machine readable medium, having stored thereon, a machine code and/or a computer program having at least one code section executable by a machine and/or a computer, thereby causing the machine and/or computer to perform the steps as described herein for providing enhanced visualization of lung sliding by automatically detecting and highlighting lung sliding in images of an ultrasound scan.

Accordingly, the present invention may be realized in hardware, software, or a combination of hardware and software. The present invention may be realized in a centralized fashion in at least one computer system, or in a distributed fashion where different elements are spread across several interconnected computer systems. Any kind of computer system or other apparatus adapted for carrying out the methods described herein is suited. A typical combination of hardware and software may be a general-purpose computer system with a computer program that, when being loaded and executed, controls the computer system such that it carries out the methods described herein.

The present invention may also be embedded in a computer program product, which comprises all the features enabling the implementation of the methods described herein, and which when loaded in a computer system is able to carry out these methods. Computer program in the present context means any expression, in any language, code or notation, of a set of instructions intended to cause a system having an information processing capability to perform a particular function either directly or after either or both of the following: a) conversion to another language, code or notation; b) reproduction in a different material form.

While the present invention has been described with reference to certain embodiments, it will be understood by those skilled in the art that various changes may be made and equivalents may be substituted without departing from the scope of the present invention. In addition, many modifications may be made to adapt a particular situation or material to the teachings of the present invention without departing from its scope. Therefore, it is intended that the present invention not be limited to the particular embodiment disclosed, but that the present invention will include all embodiments falling within the scope of the appended claims.

What is claimed is:

1. A method, comprising:
performing, by an ultrasound probe of an ultrasound system, an ultrasound scan to acquire a video clip having a plurality of images of at least a portion of a lung;
processing, by a processor of the ultrasound system, each of the plurality of images of the video clip to detect a shimmering effect in a pleura region of each of the plurality of images;
highlighting, by the processor, the detected shimmering effect as detected signs of lung sliding in each of the plurality of images of the video clip to generate a processed plurality of images; and
displaying, by a display system of the ultrasound system, at least one of the processed plurality of images as one or more of:
an enhanced virtual M mode image having a B mode image display portion and at least one M mode image display portion, wherein the B mode image display portion comprises the highlighting of the detected signs of lung sliding, and
an enhanced B mode image comprising the highlighting of the detected signs of lung sliding,
wherein the highlighting in each of the plurality of images of the video clip comprises colorizing pixels of the detected shimmering effect as the detected signs of lung sliding.

2. The method according to claim 1, wherein:
the at least one of the processed plurality of images is displayed as the enhanced virtual M mode image, and
the B mode image display portion comprises at least one virtual M mode line having a location in the B mode image display portion that corresponds with M mode image data displayed in the at least one M mode image display portion; and
comprising positioning the at least one virtual M mode line in the B mode image display portion of the enhanced virtual M mode image at one or more of:
a highlighted portion of the at least one of the processed plurality of images presented in the B mode image display portion, and a non-highlighted portion of the at least one of the processed plurality of images presented in the B mode image display portion.

3. The method according to claim 2, wherein:
the at least one virtual M mode line in the B mode image display portion of the enhanced virtual M mode image comprises two virtual M mode lines;
the at least one M mode image display portion of the enhanced virtual M mode image comprises two M mode image display portions;
a first of the two virtual M mode lines is positioned in the highlighted portion of the at least one of the processed plurality of images presented in the B mode image display portion;
first M mode image data corresponding with the location of the first of the two virtual M mode lines is displayed at a first of the two M mode image display portions;
a second of the two virtual M mode lines is positioned in the non-highlighted portion of the at least one of the processed plurality of images presented in the B mode image display portion; and
second M mode image data corresponding with the location of the second of the two virtual M mode lines is displayed at a second of the two M mode image display portions.

4. The method according to claim 1, wherein the positioning of the at least one virtual M mode line is performed automatically by the processor.

5. The method according to claim 1, wherein the positioning of the at least one virtual M mode line is performed in response to a user instruction received at a user interface device.

6. The method according to claim 1, comprising detecting, by the processor, a pleura in each of the plurality of images of the video clip, wherein the processing each of the plurality of images of the video clip to detect the shimmering effect in the pleura region is performed by analyzing pixels of each of the plurality of images of the video clip that are at one or more of the detected pleura and a region surrounding the detected pleura.

7. The method according to claim 1, comprising:
detecting, by the processor, a pleura in each of the plurality of images of the video clip; and
positioning, by the processor, a colorizing analysis box of a predefined size and shape over each of the plurality of images of the video clip based on the detected location of the pleura in each of the plurality of images.

8. The method according to claim 7, wherein the processing each of the plurality of images of the video clip to detect the shimmering effect in the pleura region is performed by analyzing pixels of each of the plurality of images of the video clip that are within the positioned colorizing analysis box.

9. The method according to claim 6, wherein the analyzing pixels is performed by one or more of:
horizontal cross correlation between consecutive images in the plurality of images of the video clip, and
computing the temporal derivative of the pixels.

10. The method according to claim 1, comprising detecting, by the processor, movement of the ultrasound probe, wherein the highlighting the detected shimmering effect as the detected signs of lung sliding is not performed in images of the plurality of images of the video clip acquired during detected movement of the ultrasound probe.

11. The method according to claim 1, comprising:
automatically selecting, by the processor, the at least one of the processed plurality of images to display by the display system as the one or more of the enhanced B mode image and the enhanced virtual M mode image, wherein the automatic selection of the at least one of the processed plurality of images to display is based on one or more of:
a detected lung point in the processed plurality of images,
a location of the detected lung point in the processed plurality of images, and
a presence of a non-highlighted portion in the processed plurality of images; and
storing the automatically selected at least one of the processed plurality of images in an archive.

12. A system, comprising:
an ultrasound device comprising:
an ultrasound probe operable to perform an ultrasound scan to acquire a video clip having a plurality of images of at least a portion of a lung;
a processor operable to:
process each of the plurality of images of the video clip to detect a shimmering effect in a pleura region of each of the plurality of images, and
highlight the detected shimmering effect as detected signs of lung sliding in each of the plurality of images of the video clip to generate a processed plurality of images; and
a display system operable to display at least one of the processed plurality of images as one or more of:
an enhanced B mode image comprising the highlight of the detected signs of lung sliding, and
an enhanced virtual M mode image having a B mode image display portion and at least one M mode image display portion, wherein the B mode image display portion comprises the highlight of the detected signs of lung sliding,
wherein the processor is operable to highlight the detected shimmering effect as the detected signs of lung sliding in each of the plurality of images of the video clip by colorizing pixels of the detected shimmering effect as the detected signs of lung sliding.

13. The system according to claim 12, wherein:
the display system is operable to display the at least one of the processed plurality of images as the enhanced virtual M mode image, wherein the B mode image display portion comprises at least one virtual M mode line having a location in the B mode image display portion that corresponds with M mode image data displayed in the at least one M mode image display portion; and
the processor is operable to position the at least one virtual M mode line in the B mode image display portion of the enhanced virtual M mode image at one or more of:
a highlighted portion of the at least one of the processed plurality of images presented in the B mode image display portion, and
a non-highlighted portion of the at least one of the processed plurality of images presented in the B mode image display portion.

14. The system according to claim 12, wherein the processor is operable to:
detect a pleura in each of the plurality of images of the video clip;
process each of the plurality of images of the video clip to detect the shimmering effect in the pleura region by analyzing pixels of each of the plurality of images of the video clip that are at one or more of the detected pleura and a region surrounding the detected pleura; and analyze the pixels by one or more of:
horizontal cross correlation between consecutive images in the plurality of images of the video clip, and
computing the temporal derivative of the pixels.

15. The system according to claim 12, wherein the processor is operable to detect movement of the ultrasound probe, and wherein the processor does not highlight the detected shimmering effect as the detected signs of lung sliding in images of the plurality of images of the video clip acquired during detected movement of the ultrasound probe.

16. The system according to claim 12, comprising an archive, wherein the processor is operable to automatically select the at least one of the processed plurality of images to store in the archive and display by the display system as the one or more of the enhanced B mode image and the enhanced virtual M mode image, and wherein the automatic selection of the at least one of the processed plurality of images to display is based on one or more of:
a detected lung point in the processed plurality of images;
a location of the detected lung point in the processed plurality of images; and
a presence of a non-highlighted portion in the processed plurality of images.

17. A non-transitory computer readable medium having stored thereon, a computer program having at least one code section, the at least one code section being executable by a machine for causing the machine to perform steps comprising:
processing each of a plurality of images of a video clip acquired by an ultrasound scan to detect a shimmering effect in a pleura region of each of a plurality of images;
highlighting the detected shimmering effect as detected signs of lung sliding in each of the plurality of images of the video clip to generate a processed plurality of images; and
displaying at least one of the processed plurality of images as one or more of:
an enhanced B mode image comprising the highlighting of the detected signs of lung sliding, and
an enhanced M mode image having a B mode image display portion and at least one M mode image display portion, wherein the B mode image display portion comprises the highlighting of the detected signs of lung sliding,
wherein the highlighting in each of the plurality of images of the video clip comprises colorizing pixels of the detected shimmering effect as the detected signs of lung sliding.

18. The non-transitory computer readable medium according to claim 17, wherein:
the at least one of the processed plurality of images is displayed as the enhanced virtual M mode image, and
the B mode image display portion comprises at least one virtual M mode line having a location in the B mode image display portion that corresponds with M mode image data displayed in the at least one M mode image display portion; and
comprising the step of positioning the at least one virtual M mode line in the B mode image display portion of the enhanced virtual M mode image at one or more of:
a highlighted portion of the at least one of the processed plurality of images presented in the B mode image display portion, and
a non-highlighted portion of the at least one of the processed plurality of images presented in the B mode image display portion.

* * * * *